(12) United States Patent
Kaib et al.

(10) Patent No.: US 10,449,378 B2
(45) Date of Patent: Oct. 22, 2019

(54) USING A WEARABLE MEDICAL DEVICE WITH MULTIPLE PATIENTS

(71) Applicant: ZOLL Medical Corporation, Chelmsford, MA (US)

(72) Inventors: Thomas E. Kaib, Irwin, PA (US); John Clark, Pittsburgh, PA (US)

(73) Assignee: ZOLL Medical Corporation, Chelmsford, MA (US)

( * ) Notice: Subject to any disclaimer, the term of this patent is extended or adjusted under 35 U.S.C. 154(b) by 125 days.

(21) Appl. No.: 15/402,420

(22) Filed: Jan. 10, 2017

(65) Prior Publication Data

US 2017/0216613 A1 Aug. 3, 2017

Related U.S. Application Data

(60) Provisional application No. 62/287,981, filed on Jan. 28, 2016.

(51) Int. Cl.
*A61N 1/39* (2006.01)
*A61B 5/00* (2006.01)
(Continued)

(52) U.S. Cl.
CPC .......... *A61N 1/3987* (2013.01); *A61B 5/0452* (2013.01); *A61B 5/14532* (2013.01);
(Continued)

(58) Field of Classification Search
CPC ............ A61N 1/37282; A61N 1/37211; A61N 1/0484; A61B 5/6804; A63B 2024/0065;
(Continued)

(56) References Cited

U.S. PATENT DOCUMENTS 5,792,190 A 8/1998 Olson et al.
5,855,592 A 1/1999 McGee et al.
(Continued)

*Primary Examiner* — Alyssa M Alter
(74) *Attorney, Agent, or Firm* — ZOLL Medical Corporation

(57) ABSTRACT

A wearable medical device comprising: a plurality of patient interface components each configured to interface with a patient; a first patient interface component of the plurality of patient interface components, the first patient interface component comprising a first sensing electrode for receiving one or more signals from a first patient, and a first therapy electrode for delivering a first treatment to the first patient; a second patient interface component of the plurality of patient interface components, the second patient interface component comprising a second sensing electrode for receiving one or more signals from a second patient; and one or more processors in communication with the plurality of patient interface components, the one or more processors configured to detect a first condition of the first patient based at least in part on the one or more signals from the first patient, cause the first treatment to be delivered to the first patient, wherein the first treatment is based at least in part on the detected first condition of the first patient, and detect a second condition of the second patient based at least in part on the one or more signals from the second patient.

21 Claims, 7 Drawing Sheets

(51) Int. Cl.
*A61B 5/0452* (2006.01)
*A61B 5/145* (2006.01)
*A61N 1/04* (2006.01)
*A61N 1/362* (2006.01)

(52) U.S. Cl.
CPC .......... *A61B 5/4836* (2013.01); *A61B 5/6804* (2013.01); *A61B 5/6805* (2013.01); *A61N 1/046* (2013.01); *A61N 1/0484* (2013.01); *A61N 1/0492* (2013.01); *A61N 1/3625* (2013.01); *A61N 1/3925* (2013.01)

(58) Field of Classification Search
CPC .... A63B 2024/0081; A63B 2024/0015; A63B 24/0075; A63B 24/0062
See application file for complete search history.

(56) References Cited

U.S. PATENT DOCUMENTS

| | | |
|---|---|---|
| 6,097,982 A | 8/2000 | Glegyak et al. |
| 9,427,564 B2 | 8/2016 | Kaib et al. |
| 2002/0107435 A1 | 8/2002 | Swetlik et al. |
| 2003/0158593 A1 | 8/2003 | Heilman et al. |
| 2005/0131465 A1 | 6/2005 | Freeman et al. |
| 2006/0253042 A1 | 11/2006 | Stahmann et al. |
| 2008/0177341 A1 | 7/2008 | Bowers |
| 2010/0036207 A1* | 2/2010 | Eckblad ................. A61B 5/162 600/300 |
| 2010/0298899 A1* | 11/2010 | Donnelly ........... A61B 5/02055 607/6 |
| 2012/0046558 A1 | 2/2012 | Virag et al. |
| 2012/0283794 A1 | 11/2012 | Kaib et al. |

\* cited by examiner

USING A WEARABLE MEDICAL DEVICE WITH MULTIPLE PATIENTS

CLAIM OF PRIORITY

This application claims priority under 35 USC § 119(e) to U.S. Patent Application Ser. No. 62/287,981, filed on Jan. 28, 2016, the entire contents of which are hereby incorporated by reference.

BACKGROUND

This disclosure relates to systems and techniques for operation of a wearable medical device.

There are a wide variety of electronic and mechanical devices for monitoring and treating patients' medical conditions. In some examples, depending on the underlying medical condition being monitored or treated, medical devices such as cardiac pacemakers or defibrillators may be surgically implanted or connected externally to the patient. In some cases, physicians may use medical devices alone or in combination with drug therapies to treat patient medical conditions.

One of the deadliest cardiac arrhythmias is ventricular fibrillation, which occurs when normal, regular electrical impulses are replaced by irregular and rapid impulses, causing the heart muscle to stop normal contractions and to begin to quiver. Normal blood flow ceases, and organ damage or death can result in minutes if normal heart contractions are not restored. Because the victim has no perceptible warning of the impending fibrillation, death often occurs before the necessary medical assistance can arrive. Other cardiac arrhythmias can include excessively slow heart rates known as bradycardia.

Implantable or external pacemakers and defibrillators (such as automated external defibrillators or AEDs) have significantly improved the ability to treat these otherwise life-threatening conditions. Such devices operate by applying corrective electrical pulses directly to the patient's heart. For example, bradycardia can be corrected through the use of an implanted or external pacemaker device. Ventricular fibrillation can be treated by an implanted or external defibrillator.

For example, certain medical devices operate by substantially continuously monitoring the patient's heart through one or more sensing electrodes for treatable arrhythmias and, when such is detected, the device applies corrective electrical pulses directly to the heart through one or more therapy electrodes.

SUMMARY

In one aspect, a wearable medical device includes a plurality of patient interface components each configured to interface with a patient. The wearable medical device also includes a first patient interface component of the plurality of patient interface components. The first patient interface component includes a first sensing electrode for receiving one or more signals from a first patient, and a first therapy electrode for delivering a first treatment to the first patient. The wearable medical device also includes a second patient interface component of the plurality of patient interface components. The second patient interface component includes a second sensing electrode for receiving one or more signals from a second patient. The wearable medical device also includes one or more processors in communication with the plurality of patient interface components. The one or more processors are configured to detect a first condition of the first patient based at least in part on the one or more signals from the first patient. The processors are also configured to cause the first treatment to be delivered to the first patient. The first treatment is based at least in part on the detected first condition of the first patient. The processors are also configured to detect a second condition of the second patient based at least in part on the one or more signals from the second patient.

Implementations can include one or more of the following features.

In some implementations, the wearable medical device includes a garment for affixing the first patient interface component to the body of the first patient. The garment includes a compartment configured for storing the second sensing electrode.

In some implementations, the second patient interface component includes a second therapy electrode for delivering a second treatment to the second patient.

In some implementations, the wearable medical device includes a garment for affixing the first patient interface component to the body of the first patient. The garment includes a compartment configured for storing the second sensing electrode and the second therapy electrode.

In some implementations, the wearable medical device includes a medical device controller that includes the one or more processors.

In some implementations, the medical device controller includes a port for connecting the plurality of patient interface components to the medical device controller.

In some implementations, the wearable medical device includes a distribution node that includes a patient interface processor. The distribution node is configured to connect to the port.

In some implementations, each of the plurality of patient interface components is configured to connect to the distribution node.

In some implementations, the patient interface processor is configured to facilitate communication between the plurality of patient interface components and the one or more processors of the medical device.

In some implementations, the plurality of patient interface components and the one or more processors of the medical device communicate using a predetermined interface protocol.

In some implementations, the predetermined interface protocol is a controller area network (CAN) protocol.

In some implementations, the port includes a CAN bus.

In some implementations, the patient interface processor is configured to process the one or more signals received by the sensing electrodes.

In some implementations, the patient interface processor is configured to cause a conductive gel to be released by the therapy electrode prior to the first treatment being delivered to the first patient.

In some implementations, the patient interface processor is configured to provide an alert to the first patient prior to the first treatment being delivered to the first patient.

In some implementations, the first patient interface component is configured to connect to the port, and a remainder of the plurality of patient interface components are configured to connect to the first patient interface component in series.

In some implementations, the medical device controller includes a plurality of ports, each port for connecting one or more the plurality of patient interface components to the medical device controller.

In some implementations, each patient interface component includes a patient interface processor.

In some implementations, each patient interface component includes a therapy electrode for delivering a treatment to a corresponding patient.

In some implementations, each patient interface component includes one or more capacitors for storing electrical energy for use by the corresponding therapy electrode for delivering the corresponding treatment to the corresponding patient.

In some implementations, each patient interface processor is configured to provide an alert to the corresponding patient prior to the treatment being delivered to the corresponding patient.

In some implementations, the alert is a haptic alert.

In some implementations, the wearable medical device includes a plurality of garments, each garment for affixing one of the plurality of patient interface components to the body of a corresponding patient.

In some implementations, the wearable medical device includes an electrode patch that includes the first sensing electrode and the first therapy electrode.

In some implementations, one or both of the first and second conditions include a cardiac condition.

In some implementations, one or both of the first and second conditions include an arrhythmia condition.

In some implementations, one or both of the first and second conditions include an abnormal blood sugar content.

In some implementations, the first treatment includes a defibrillation current or one or more pacing pulses.

In some implementations, the second treatment includes a defibrillation current.

In some implementations, at least one of the electrodes is disposable.

In some implementations, the wearable medical device includes a user interface configured for receiving input and providing information related to one or both of the first condition and the first treatment, and receiving input and providing information related to one or both of the second condition and the second treatment.

In some implementations, the user interface is configured for providing the information related to one or both of the second condition and the second treatment when the second patient interface component is in communication with the one or more processors.

Implementations can include one or more of the following advantages.

In some implementations, the wearable medical device can be used to monitor and/or treat the first patient (e.g., a patient fitted with the wearable medical device) as well as one or more additional patients. For example, during normal use, the first patient may encounter the second patient (e.g., a stranger who the first patient happens to come across by chance while out in public. The first patient may encounter the stranger on the ground who appears to be unconscious, or the stranger may be exhibiting other signs typically associated with a cardiac event. The first patient can use the second patient interface component to monitor the stranger for a potential cardiac condition and/or treat the stranger for a detected cardiac condition.

In some implementations, the wearable medical device may be configured to monitor and/or treat multiple patients concurrently. For example, the wearable medical device may be configured to monitor and/or treat the first patient while monitoring and/or treating one or more additional patients (e.g., without requiring the first patient to remove the wearable medical device).

In some implementations, the wearable medical device is configured to accept a plurality of patient interface components that are each configured to monitor and/or treat a corresponding patient. The wearable medical device may be configured to accept connections to additional patient interface components for treating even more patients. The wearable medical device can include one or more patient interface processors that are configured to facilitate communication between the patient interface components and the processor of the medical device controller. The patient interface processors may also be configured to handle the routing of power and/or control signals between the medical device controller and the patient interface components.

Other features and advantages of the invention will be apparent from the drawings, detailed description, and claims.

DESCRIPTION OF DRAWINGS

The accompanying drawings are not intended to be drawn to scale. In the drawings, components that are identical or nearly identical may be represented by a like numeral. For purposes of clarity, not ever component is labeled in every drawing. In the drawings.

DETAILED DESCRIPTION

Figure 1:
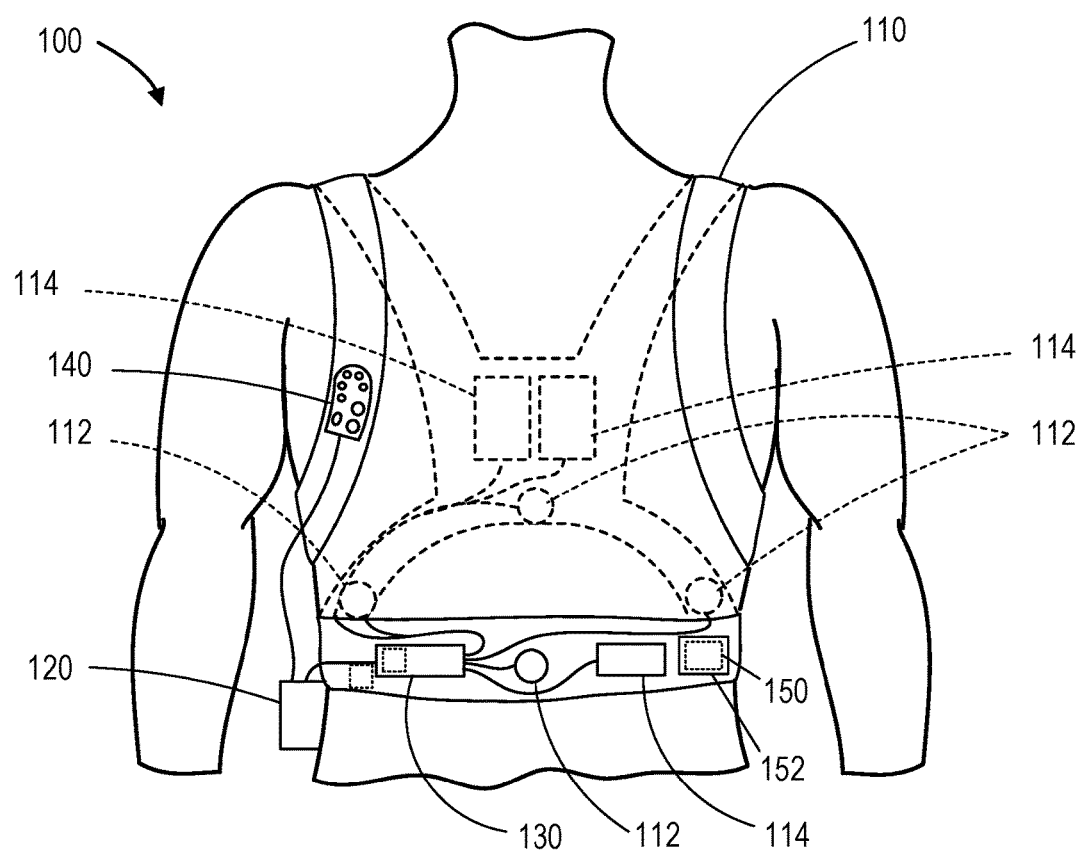
FIG. 1 is an example of a wearable medical device that includes a garment, a medical device controller, and a distribution node.

A medical device for use with the systems and techniques as disclosed herein can be configured to monitor and/or treat multiple patients. For example, the medical device can be configured to monitor physiological signals from multiple patients at substantially the same time, and on detecting a medical event based on the monitored signals, treat one or more of the multiple patients as needed. For example, a first patient fitted with a medical device as described herein may use his or her device to monitor a second patient or multiple patients (e.g., including the first patient) at substantially the same time. If any of the patients experiences a medical condition detected by the device, the medical device can be configured to treat the patient in response to the detected condition. The device can then return to monitoring the multiple patients and be available to treat the same or a different patient as needed. Further, the device can issue treatment to multiple patients at substantially the same time (e.g., initiate a first treatment sequence for a first patient and a second treatment sequence for a second patient, where the first and second treatment sequences may substantially overlap in time). As described herein, a treatment sequence can include detecting a treatable medical condition, preparing the device for the treatment of the condition, providing a notification to the patient and/or others about an impending treatment, and/or delivering the treatment when certain conditions are met. For example, in the case of a wearable defibrillator, the treatment sequence may include charging the energy storage module of the device in preparation for delivering a shock to a patient, providing a warning or notification to the patient, releasing conductive gel on to the patient's skin, instructing the patient to respond or otherwise indicate that the patient is conscious, and if no response is recorded, delivering the shock to the patient. In some implementations, depending on the situation and the patient's condition and response, the treatment sequence can take between approximately 30 seconds and 2 minutes. In some examples, the treatment sequence may be shorter or longer than this period.

The medical device may be an ambulatory device (e.g., a device that is capable of and designed for moving with the first patient as the first patient goes about his or her daily routine). In some examples, the medical device can be configured as a wearable defibrillator worn by the first patient, such as the LifeVest® wearable defibrillator available from ZOLL® Medical Corporation of Chelmsford, Mass. The physiological signals monitored by the device can include cardiac signals (e.g., ECG signals, heart sound signals, and other cardiac-related physiological signals) and/or other signals of one or more patients as described in more detail below.

The wearable defibrillator may include a garment worn by the first patient to which sensing and therapy electrodes are affixed for determining whether the first patient may be experiencing a condition, such as a cardiac condition, and causing an appropriate treatment to be applied to the first patient. The wearable defibrillator can also include additional sensing electrodes for determining whether one or more additional patients may be experiencing a cardiac condition, and/or additional therapy electrodes for causing appropriate treatments to be applied to the one or more additional patients.

In some implementations, the medical device can be used as a cardiac monitor for the first patient and/or one or more of the additional patients, and transmit cardiac information in a manner similar to those employed in mobile cardiac telemetry (MCT) and/or continuous event monitoring (CEM) applications.

In some implementations, the medical device can be configured to determine an appropriate treatment for the patient based on the sensed cardiac signals and cause one or more therapeutic shocks (e.g., defibrillating and/or pacing shocks) to be delivered to the body of the first patient and/or one or more of the additional patients. The medical device can include a plurality of therapy electrodes that are disposed at various locations of the first patient's body and configured to deliver the therapeutic shocks. The medical device can also include same or similar therapy electrodes for disposing on one or more locations of one or more of the other patients' bodies.

In some implementations, the electrodes for monitoring and/or treating the second patient are configured to connect to the medical device via one or more interfaces (e.g., ports) on the medical device. The interface may allow the electrodes to communicate with the medical device according to a predetermined interface protocol. The predetermined interface protocol may be a controller area network (CAN) protocol.

In some implementations, the medical device can be configured to monitor and/or treat additional patients (e.g., a third patient, a fourth patient, etc.) using additional sensing electrodes and/or therapy electrodes. The medical device can include multiple interfaces (e.g., ports) to which various sets of electrodes can be connected. For example, multiple sets of one or more electrodes can be configured to connect to a corresponding port on the medical device, with each set of one or more electrodes for treating a corresponding patient.

In some implementations, multiple sets of one or more electrodes may be configured to connect to the medical device via a single interface on the medical device. For example, a second set of one or more electrodes (e.g., for the second patient) may be configured to connect to a port on the medical device, a third set of one or more electrodes (e.g., for the third patient) may be configured to connect to the first set, a fourth set of one or more electrodes (e.g., for the fourth patient) may be configured to connect to the third set, etc., such that the sets of one or more electrodes are connected to the medical device in series. In some implementations, the port to which the first set of one or more electrodes connects is a CAN bus, and the sets of one or more electrodes connected in series are configured to communicate with the medical device using a CAN protocol.

In some examples, a patient interface component can be configured to interface with a patient, e.g., via one or more sensing electrode and/or one or more therapy electrode for monitoring and/or providing treatment to the patient. In this manner, each of the sets of one or more electrodes can be included within such a patient interface component.

Further, the patient interface component may include one or more of the following additional components: a patient interface controller, an alarm module for providing alerts and alarms to the monitored patient, conductive gel receptacles disposed proximate to one or more electrodes (e.g., the therapy electrodes) for deploying conductive gel to improve a conductive path between an electrode and the patient's skin, an energy storage module (e.g., one or more capacitors) for supplying therapeutic pulses to the monitored patient and associated circuitry, one or more batteries for providing energy to the energy storage module and associated circuitry, and converter circuitry for connecting the battery to the energy storage module. In some implementations, each patient interface component can be configured to interface with multiple patients. For example, one or more of the patient interface components can each include a processor (e.g., the patient interface processor) configured to execute instructions in accordance with the methods described herein. For example, the patient interface processor can be configured to facilitate communication between the plurality of patient interface components and a processor of the medical device. For example, the patient interface processor can allow the plurality of patient interface components to communicate with the medical device using the CAN protocol.

In some implementations, the patient interface processor is included in a distribution node that is configured to connect to the port on the medical device. For example, the distribution node, including the patient interface processor, may be configured to connect to the port on the medical device, and the plurality of patient interface components may be configured to connect to the distribution node. In this way, the patient interface processor can facilitate communication (e.g., using the CAN protocol) between the plurality of patient interface components and the medical device. In some implementations, one or more of the patient interface components can include a local energy storage module (e.g., including one or more capacitors) as well as all or a portion of associated pulse delivery circuitry configured to store and discharge electrical energy for delivering treatments to corresponding patients.

In some implementations, the patient interface components may be controlled via control signals from a medical device controller. For example, if the situation arises, such control signals can direct one or more battery disposed in a patient interface component to charge its corresponding capacitors for delivering therapy pulses to the patient via one or more therapy electrodes. In some implementations, instead of or in addition to the controller, a patient interface processor as described herein may execute the treatment sequence (including alarms and charge delivery). The patient interface processor may be configured to split operations with the controller. As an example, the patient interface processor may be configured to manage the acquisition and preprocessing of ECG signals received from the patient, while the controller may include logic for receiving the incoming ECG signals and determining whether a treatable cardiac condition exists that merits providing therapeutic shocks to the monitored patient.

The medical device can be configured to monitor a patient (e.g., the first patient and/or additional patients) for an arrhythmia condition such as bradycardia, ventricular tachycardia (VT) or ventricular fibrillation (VF), among others. Bradycardia, also known as bradyarrhythmia, is a slow heart rate (e.g., in some implementations, a slow resting heart rate of under 60 beats per minute in adults), which can result in fatigue, weakness, dizziness, and potentially fainting. While the detection methods and systems described hereinafter are disclosed as detecting VT and VF, this is not to be construed as limiting the invention. Other arrhythmias, such as, but not limited to, atrial arrhythmias such as premature atrial contractions (PACs), multifocal atrial tachycardia, atrial flutter, and atrial fibrillation, supraventricular tachycardia (SVT), junctional arrhythmias, tachycardia, junctional rhythm, junctional tachycardia, premature junctional contraction, and ventrical arrhythmias such as premature ventricular contractions (PVCs) and accelerated idioventricular rhythm, may also be detected. In some implementations (e.g., implementations in which the medical device is a treatment device, such as a pacing and/or a defibrillating device), if an arrhythmia condition is detected, the medical device can automatically provide a pacing or defibrillation pulse or shock to treat the condition.

In some implementations, the medical device may be configured to monitor one or more patients for a treatable cardiac condition. In this regard, the device may be configured to obtain a baseline ECG recording for each patient to be monitored by the device. For example, the device may be initially configured with baseline ECG recordings for persons who associate with a primary patient wearing the medical device and who may, in the event of an emergency, need to be monitored by the device (e.g., the primary patient's family members). For example, such baseline ECG recordings may be obtained during initial setup of the device. In some examples, the medical device may be configured to obtain and store ECG recordings corresponding to all persons in a household. The ECG recordings can be refreshed (e.g., re-recorded) at certain configurable periodic or aperiodic time intervals. For example, a baseline ECG recording may have a length of approximately 30 seconds to one minute, although recordings of longer or shorter length may be obtained. In the event that the primary patient needs to deploy the device to monitor and/or treat another patient, the device can be configured to provide alarm, alerts, and/or other information relating to a treatment sequence to either the primary patient as the device operator or the monitored patient, or both.

In operation, the medical device may include an axis analyzer to derive a signal representation of the electrical axis of the heart of a monitored patient from whom ECG signals are received. In some implementations, the baseline ECG values are fed into the analyzer in the form of filter coefficient values corresponding to the filters used in the analyzer. Changes in the signal representation of the electrical axis of the heart can be evaluated to determine whether a treatable condition exists (e.g., the patient is experiencing a cardiac condition). For example, the signal representation can include a magnitude component and a phase component. In some examples, the phase component can indicate a zero-crossing indication. In some implementations, the analyzer can use a complex matched filter to analyze the ECG signals.

A treatable condition can be determined based on changes in the heart axis information from the monitored patient's baseline values as determined from the patient's baseline ECG recording. In particular, one or more specific comparisons of an incidence of zero phase crossing with periods of peaks of the magnitude component of the heart axis representation can be used to indicate the treatable condition. When the analyzer determines that a treatable condition exists (e.g., the patient is experiencing a cardiac condition), the analyzer can set a flag to indicate the condition. Additional details concerning a method for determining treatable conditions are disclosed in U.S. Pat. No. 5,944,669 (the "'669 patent") entitled "Apparatus and method for sensing cardiac function," the contents of which are incorporated by reference herein in its entirety.

In some implementations, once the baseline filter coefficient values are input to the analyzer, the analyzer continuously monitors the phase component for zero crossing conditions and when detected, the analyzer checks the magnitude component to determine whether the magnitude component is also above a magnitude threshold value. For example, the magnitude threshold value may be automatically calculated based on a prior history of the signal. Because amplitudes can vary according to a quality of the signal, the magnitude threshold value is allowed to vary within a preset of programmable range of values. In an example, the magnitude threshold value can be set to less than 90% of a previously detected peak level of the magnitude component.

After it is determined that a monitored patient may be experiencing a cardiac condition, the medical device can be configured to select a treatment sequence for treating the particular condition. For example, the medical device may be configured to determine that a series of defibrillation shocks at particular intensities is appropriate for treating the particular cardiac condition. In some implementations, the device can issue up to five bi-phasic shocks if the device determines that the cardiac condition is present after each preceding shock. The device can issue more or fewer shocks to the patient as the situation may require.

The medical device may provide one or more indications (e.g., warnings or alerts) to the monitored patient or other device operator that a treatment shock is about to be delivered before it is actually delivered to the monitored patient. The one or more indications may be in various forms. For example, one or more indications may be haptic (e.g., activation of a vibration alarm placed in proximity to the primary or the monitored patient's skin), and one or more indications may be audible. In some implementations, a first indication is a haptic indication that is intended to attract the attention of the device operator or the monitored patient without disturbing others, a second indication is a low volume audible alert, and a third indication is a high volume audible alert. In some implementations, one or more of the indications may be issued by a connection pod (e.g., a distribution node 130) as described in more detail below.

On perceiving the alert, the monitored patient or device operator may be able to instruct the medical device to refrain from delivering the treatment shock. For example, the monitored patient or the device operator may instruct the medical device to refrain from applying a treatment shock if the monitored patient is well and the medical device falsely identified a cardiac event. The medical device can include a user interface for interacting with the medical device. For example, the medical device can include one or more input mechanisms (e.g., buttons) that the monitored patient or device operator can interact with in order to respond to the alert. For example, if the monitored patient or the operator does not respond to the treatment alert (e.g., by holding down one or more response buttons) within a predetermined amount of time, the medical device can deliver the treatment shock to restore the monitored patient's normal heart rhythm.

As mentioned above, in some implementations, the medical device can be configured to monitor one or more cardiac signals of one or more additional patients and determine whether each additional patient may be experiencing a cardiac condition. For example, the medical device can include additional sets of one or more electrodes that are configured to monitor and/or treat the additional patients, as described in more detail below. In this way, exposure of the life-saving capabilities of the medical device are maximized.

The medical device is capable of continuously, substantially continuously, long-term and/or extended use or wear by, or attachment or connection to one patient, and further capable of monitoring and/or treating additional patients.

The medical device is configured to continuously or substantially continuously monitor a patient for cardiac-related information (e.g., ECG information, including arrhythmia information, heart sounds, etc.) and/or non-cardiac information (e.g., blood oxygen, the patient's temperature, glucose levels, tissue fluid levels, and/or lung sounds).

The medical device may carry out its monitoring in periodic or aperiodic time intervals or times. For example, the monitoring during intervals or times can be triggered by a user action or another event. For example, one or more durations between the periodic or aperiodic intervals or times can be user-configurable.

The medical device can be a hospital based medical device including, for example, a cardiac monitoring device, a defibrillator, and/or a pacing device. For example, the hospital based device can include a defibrillator and/or a pacing device configured for continuous or substantially continuous use, wear, connection, attachment, or monitoring by/to/of a patient in a hospital environment. The hospital based device can include a plurality of therapy and sensing electrodes that are attached to the patient's skin. In some examples, the sensing and/or therapy electrodes are disposable adhesive electrodes. In some implementations, the electrodes are affixed to an electrode assembly (e.g., a patch), which can then be adhesively attached to the patient's skin. The sensing and/or therapy electrodes, and/or integrated electrodes can be attached to the patient's skin at particular locations as prescribed by a trained professional. In some implementations, the medical device can be affixed to patients via integrated electrode patches that include both sensing electrodes and therapy electrodes for providing both sensing and treatment functions in a single component.

Example Wearable Medical Device

FIG. 1 illustrates an example wearable medical device 100. The wearable medical device 100 includes a plurality of sensing electrodes 112 that can be disposed at various positions about the patient's body. The sensing electrodes 112 are electrically coupled to a medical device controller 120 through a connection pod such as a distribution node 130. In some implementations, some of the components of the wearable medical device 100 are affixed to a garment 110 that can be worn on the patient's torso. For example, as shown in FIG. 1, the sensing electrodes 112 and distribution node 130 can be assembled or integrated into the garment 110 as shown. The sensing electrodes 112 are configured to monitor the cardiac function of the patient (e.g., by monitoring one or more cardiac signals of the patient). While FIG. 1 shows three sensing electrodes 112, fewer or additional sensing electrodes may be provided, and the plurality of sensing electrodes 112 may be disposed at various locations about the patient's body. The controller 120 can be mounted on or attached to a belt worn by the patient.

The wearable medical device 100 can also optionally include a plurality of therapy electrodes 114 that are electrically coupled to the medical device controller 120 through the distribution node 130. The therapy electrodes 114 are configured to deliver one or more therapeutic defibrillating shocks to the body of the patient if it is determined that such treatment is warranted. The distribution node 130 may include electronic circuitry and one or more sensors (e.g., a motion sensor, an accelerometer, etc.) that are configured to monitor patient activity. In some implementations, the wearable medical device 100 may be a monitoring only device that omits the therapy delivery capabilities and associated components (e.g., the therapy electrodes 114). In some implementations, various treatment components may be packaged into various modules that can be attached to or removed from the wearable medical device 100 as needed.

The controller 120 can include one or more response buttons (e.g., 210 of FIGS. 4 and 5A-5B) and a user interface such as a touch screen (e.g., 220 of FIGS. 4 and 5A-5B) that the patient can interact with in order to communicate with the medical device 100. The controller 120 can also include a speaker (e.g., 230 of FIGS. 4 and 5A-5B) for communicating information to the primary patient wearing the medical device 100, other patients, and/or bystanders. In some examples, when the controller 120 determines that the patient is experiencing cardiac arrhythmia, the speaker can issue an audible alarm to alert the patient and bystanders to the patient's medical condition. In some examples, the controller 120 can instruct the patient to press and hold one or both of the response buttons on the medical device controller 120 to indicate that the patient is conscious, thereby instructing the medical device controller 120 to withhold the delivery of one or more therapeutic defibrillating shocks. If the patient does not respond to an instruction from the controller 120, the medical device 100 may determine that the patient is unconscious and proceed with the treatment sequence, culminating in the delivery of one or more defibrillating shocks to the body of the patient.

As briefly described above, the sensing electrodes 112 and the therapy electrodes 114 are included in a first patient interface component that is configured to interface with the patient who is wearing the garment 110 (e.g., the first patient).

The wearable medical device 100 is also configured to monitor one or more cardiac signals of at least one additional patient (e.g., a second patient additional to the first patient wearing the wearable medical device 100) and determine whether the second patient may be experiencing a cardiac condition. For example, the wearable medical device 100 can include an additional set of one or more electrodes (e.g., different electrodes than the sensing electrodes 112 and the therapy electrodes 114 used for monitoring and treating the first patient) that are configured to monitor and/or treat the second patient. The additional set of one or more electrodes are included in a second patient interface component 150 that is configured to interface with the second patient.

At least a portion of the second patient interface component 150 can be stored in a compartment of the garment 110. The compartment 152 may be a pocket or pouch that is sewn into the garment 110. The compartment 152 may include a mechanism for closing the compartment 152, such as a zipper or a hook-and-loop fastener. The second patient interface component 150 includes one or more sensing electrode for monitoring cardiac signals of the second patient and determining whether the second patient may be experiencing a cardiac condition. The second patient interface component 150 can also optionally include one or more therapy electrodes for applying an appropriate treatment to the second patient that is based on the sensed cardiac signals.

The second patient interface component 150 may be connected to or disconnected from the controller 120 (e.g., via the distribution node 130) while the second patient interface component 150 resides in the compartment 152. For example, the compartment 152 may be configured to allow wires to run from the second patient interface component 150 to the distribution node 130 while the second patient interface component 150 resides in the compartment (e.g., through a slit in the compartment 152 and/or another portion of the garment 110). In some examples, the second patient interface component 150 is disconnected from the distribution node 130 while the second patient interface component 150 resides in the compartment 152, and the second patient interface component 150 can be connected to the distribution node 130 when it is needed.

Figure 2:
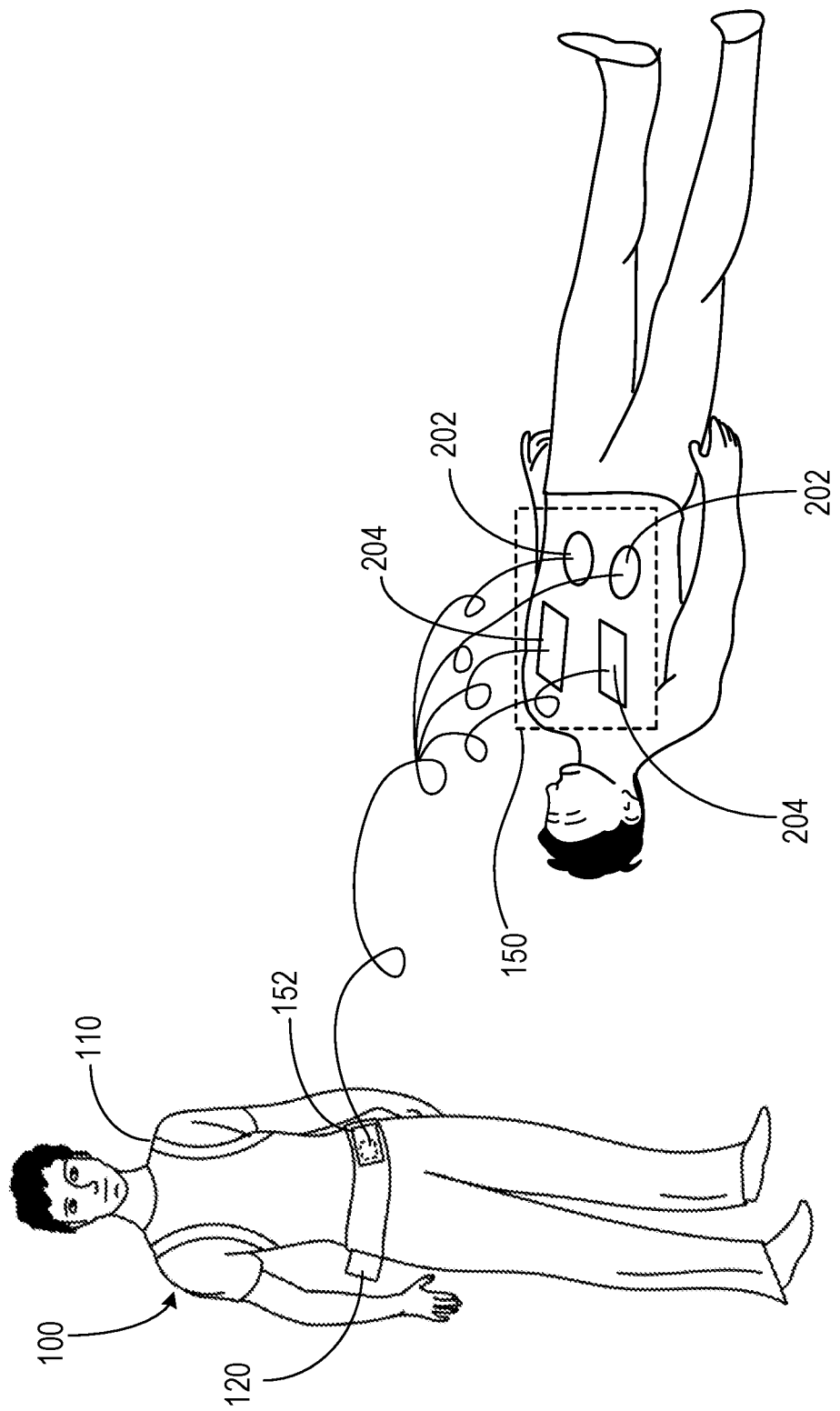
FIG. 2 shows an example of the wearable medical device of FIG. 1 being used to treat a second patient.

FIG. 2 shows an example of the second patient interface component 150 of the wearable medical device 100 being used to treat a second patient. During normal use, the first patient may encounter a second patient who may be experiencing a cardiac event. The second patient may be a stranger who the first patient happens to come across by chance (e.g., while out in public). For example, the first patient may be at a shopping mall and encounter a stranger on the ground who appears to be unconscious, or the stranger may be exhibiting other signs typically associated with a cardiac event. The first patient can remove the second patient interface component 150 from the compartment 152 of the garment 110. The second patient interface component 150 includes sensing electrodes 202 for monitoring cardiac signals of the second patient and determining whether the second patient may be experiencing a cardiac condition. In this example, the second patient interface component 150 also includes therapy electrodes 204 for applying an appropriate treatment to the second patient that is based on the sensed cardiac signals.

Once removed from the compartment 152, the first patient can affix the sensing electrodes 202 of the second patient interface component 150 to the second patient. If the second patient interface component 150 is not already connected to the controller 120 (e.g., via the distribution node 130), the first patient can establish this connection. The sensing electrodes 202 can then begin collecting cardiac signals from the second patient. In some implementations, commencement of the collection of the cardiac signals may begin automatically upon the sensing electrodes 202 being affixed to the second patient. In some implementations, commencement of the collection of the cardiac signals may begin upon the wearable medical device 100 receiving an input from the first patient (e.g., via a user interface of the controller 120, such as via the touch screen 220).

Based on the cardiac signals received from the second patient, the controller 120 monitors the cardiac activity of the second patient and identifies whether the second patient may be experiencing a cardiac event. If the second patient is experiencing a cardiac event, the controller 120 may determine an appropriate treatment for treating the particular cardiac event. If the second patient interface component 150 includes the optional therapy electrodes 204, the therapy electrodes 204 may be affixed to the second patient for delivering the treatment. In some implementations, the therapy electrodes 204 are affixed to the second patient at the same time that the sensing electrodes 202 are affixed. The treatment can then be applied to the second patient. In some examples, the treatment is applied upon the wearable medical device 100 receiving an input from the first patient. The treatment may be preceded with a warning, and/or the treatment may require a confirmation from the first patient before it is applied to the second patient.

One or more of the patient interface components can include a local energy storage module (e.g., including one or more capacitors) along with some or all of the associated energy delivery circuitry for storing and discharging electrical energy for delivering treatments to corresponding patients. For example, the second patient interface component 150 can include one or more capacitors for storing electrical energy for use by the therapy electrodes 204 for delivering treatments to the second patient. Thus, sufficient energy for delivering treatments is available on demand. In this way, treatments can be applied immediately in situations in which even a minimal delay may be catastrophic.

In some implementations, information related to the detected cardiac event and/or the appropriate treatment may be transmitted to a third party such as emergency medical services. For example, the information can be transmission to a server, such as a remote medical server, where medical professionals can analyze the information and take appropriate action. If a treatment is applied to the second patient via the therapy electrodes 204 of the second patient interface component 150, a status and results of such treatment may also be transmitted. The transmissions may occur continuously, at fixed intervals, or upon occurrences of particular events, among others.

In some implementations, the first patient may remove the wearable medical device 100 from himself or herself before attending to the second patient. For example, the first patient may remove the wearable medical device 100 to make it easier to affix the electrodes of the second patient interface component 150 to the second patient. In some implementations, one or more functions of the wearable medical device 100 may be suspended and/or disabled while the wearable medical device 100 is being used to monitor and/or treat the second patient. For example, the wearable medical device 100 may temporarily suspend monitoring functions related to the first patient while the second patient is being monitoring for occurrence of a cardiac event. In some examples, the wearable medical device 100 may temporarily suspend treatment functions related to the first patient while treatments are being applied to the second patient. In some implementations, monitoring and treatment functions related to all patients of the wearable medical device 100 remain operational at all times. That is, the wearable medical device 100 may be configured to monitor and/or treat both the first patient and the second patient simultaneously.

While the wearable medical device 100 described with references to FIGS. 1 and 2 has been largely described as being configured to monitor and/or treat a first patient and a second patient, the wearable medical device 100 may be configured to monitor and/or treat any number of patients. That is, the wearable medical device 100 may include additional patient interface components each configured to monitor and/or treat one or more additional patients.

The first patient interface component (e.g., including the sensing electrodes 112 and the therapy electrodes 114) and the second patient interface component 150 are connected to the controller 120 via the distribution node 130. In some implementations, the controller 120 includes an interface, e.g., a port, such as the port 402 of FIGS. 4A-4B, that is configured to receive (e.g., connect to) the distribution node 130. In this way, the first patient interface component and the second patient interface component can removably connect to the controller 120 via the distribution node 130 and the port.

Figure 3:
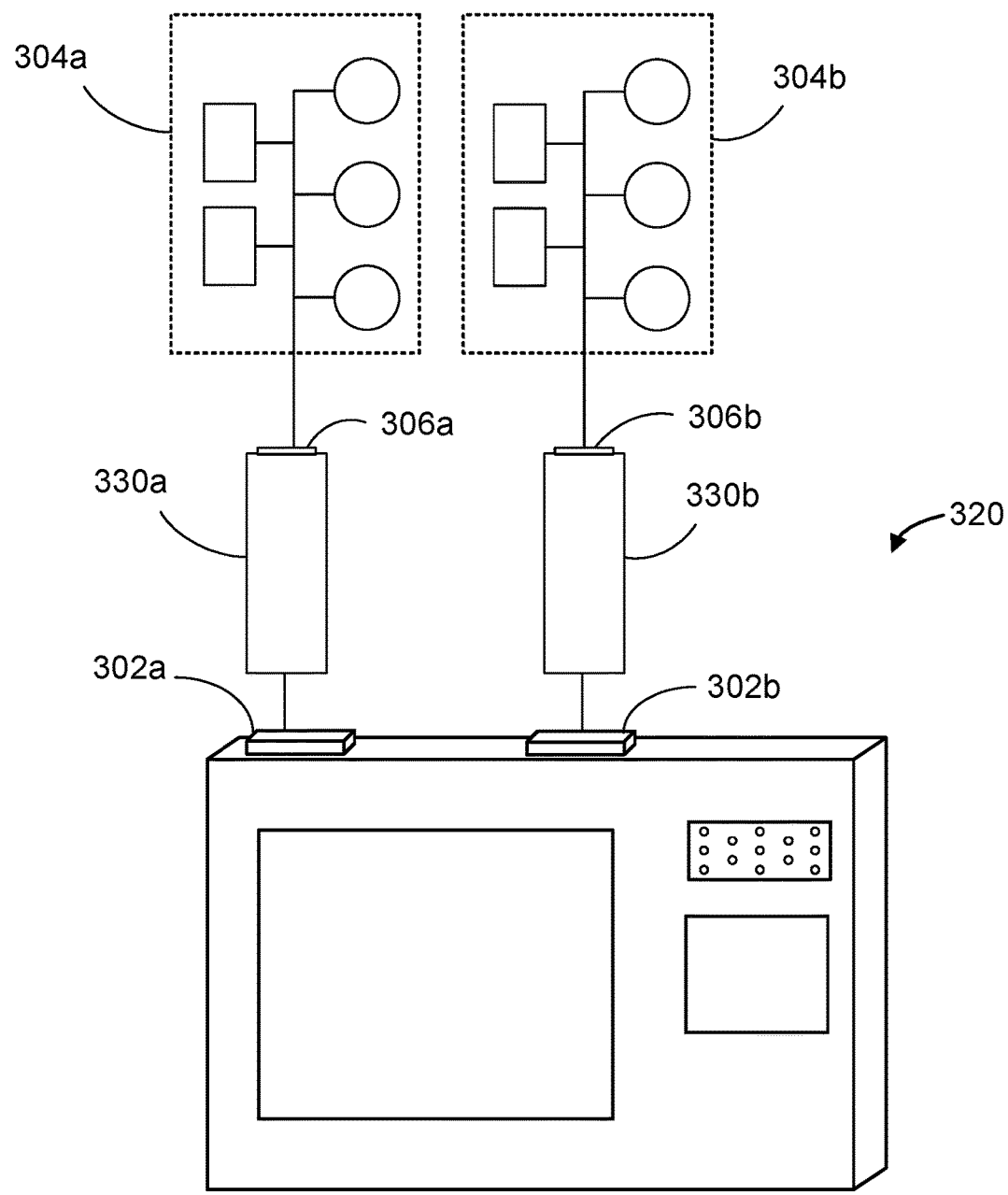
FIG. 3 shows another example of a medical device controller that includes multiple ports.

In some implementations, the medical device controller may include multiple ports to which patient interface components can be connected. FIG. 3 shows another example of a medical device controller 320 that includes multiple ports 302a, 302b, and so on, to which multiple patient interface component 304a, 304b, and so on, can be connected via a corresponding distribution node 330a, 330b. For example, a first distribution node 330a can be connected to a first port 302a on the controller 320, and the first patient interface component 304a can be connected to a port 306a on the first distribution node 330a; a second distribution node 330b can be connected to a second port 302b on the controller 320, and the second patient interface component 304b can be connected to a port 306b on the second distribution node 330b, and so on. The controller 320 may be substantially similar to the controller 120 of FIGS. 1 and 2. While only two ports 302a, 302b, two distribution nodes 330a, 330b, and two patient interface components 304a, 304b are shown in FIG. 3, the controller 320 can include any number of ports, any number of distribution nodes, and any number of patient interface components. Each patient interface component can be configured to connect to a corresponding port on the controller 320 via a corresponding distribution node.

In some implementations, one or more of the distribution nodes, including the first and second distribution nodes 330a, 330b, may include additional ports to which additional patient interface component may be connected. Each of the distribution nodes may include a processor (e.g., a patient interface processor) for facilitating communication between connected patient interface components and a processor of the controller 320 (e.g., the processor 518 of FIG. 5). In some implementations, the second distribution node 330b may include a second port to which a third patient interface component can be connected, and a patient interface processor of the second distribution node 330b may be configured to facilitate communication between the second patient interface component 304b, the third patient interface component, and the processor of the controller 320.

In some implementations (e.g., implementations in which the patient interface component includes therapy electrodes), one or more of the patient interface components 304a, 304b may include one or more capacitors as well as some or all of the associated circuitry for storing electrical energy for use by the corresponding therapy electrodes for delivering treatments to the corresponding patients. Thus, sufficient energy for delivering one or more treatments is available on demand. In this way, treatment can be applied immediately in situations in which even a minimal delay may be catastrophic.

In some implementations, one or more of the distribution nodes, including the first and second distribution nodes 330a, 330b, may be configured to accept connections to additional patient interface components in series. Each of the distribution nodes may include a processor (e.g., a patient interface processor) for facilitating communication between connected patient interface components and the processor 518 of the controller 320. For example, in some implementations, the second patient interface component 304b may be connected to the second distribution node 330b via the port 306b, and a third patient interface component may be connected to the second patient interface component 304b via a port on the second patient interface component 304b, as described in more detail below.

In some implementations, each patient interface processor can be configured to cause an alert to be provided by the corresponding patient interface component 304a, 304b or corresponding distribution node 330a, 330b. For example, the patient interface processor may be configured to cause the corresponding distribution node 330a, 330b to provide an alert prior to a treatment being applied to the corresponding patient (e.g., the first patient and the second patient). In this regard, each patient interface component 304a, 304b, or each distribution node 330a, 330b can include a speaker for providing an audio alert and/or a vibration motor for providing a haptic alert.

Figure 4A:
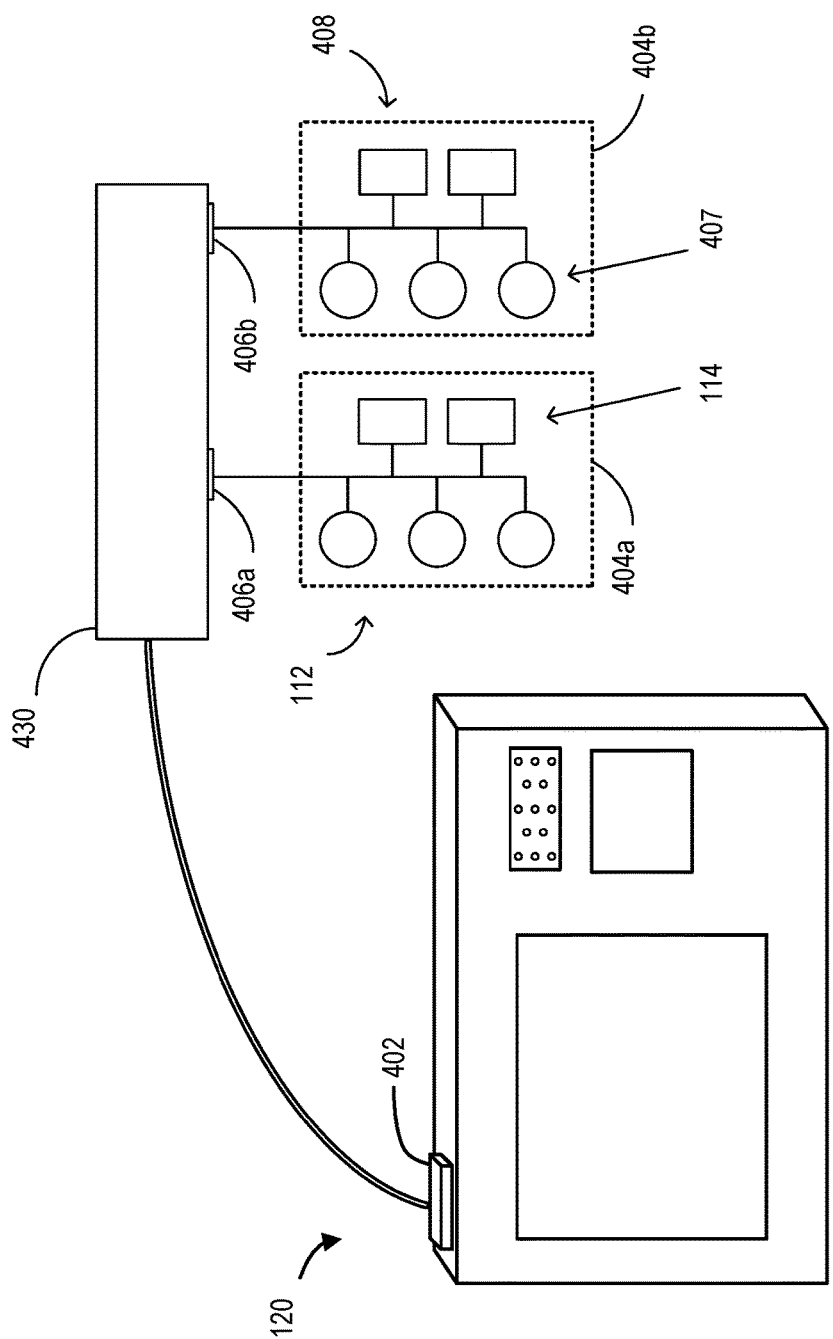
FIGS. 4A-4B show an example of the medical device controller of FIGS. 1 and 2.

In some implementations, the medical device controller 120 may include a single port to which patient interface components can be connected. FIG. 4A shows an example of two patient interface components 404a, 404b connected to the medical device controller 120 via a distribution node 430 with multiple ports 406a, 406b. The distribution node 430 is connected to the port 402 of the controller 120, and the patient interface components 404a, 404b are connected to the distribution node 430 via the two ports 406a, 406b. In some examples, power and/or control signals may be routed from the controller 120 to the patient interface components 404a, 404b through the ports 406a, 406b.

In some implementations, the controller 120 or a patient interface processor may direct a patient interface component 404a, 404b to initiate the charging of the capacitors from batteries that may be disposed on the patient interface component 404a, 404b. In some implementations, the power for charging the capacitors may be routed from batteries associated with the controller 120 and through the ports 406a, 406b.

In this example, the distribution node 430 includes two ports 406a, 406b for connecting the two patient interface components 404a, 404b. However, the distribution node 430 can include any number of ports for connecting any number of patient interface components. The sensing electrodes 112 and the therapy electrodes 114 for interfacing with the first patient (e.g., the patient who is wearing the wearable medical device 100) are included in the first patient interface component 404a, and sensing electrodes 407 and optional therapy electrodes 408 for interfacing with a second patient are included in the second patient interface component 404b. In some implementations, the second patient interface component 404b is configured to monitor the second patient without providing treatment capabilities, and thus the second patient interface component 404b may omit the therapy electrodes 408. The first patient interface component 404a can be affixed to the garment 110 such that the electrodes 112, 114 are appropriately positioned on the first patient when the first patient is wearing the garment 110. At least a portion of the second patient interface component 404b may be stored in the garment 110, as described above with reference to FIG. 1.

In some implementations, the distribution node 430 includes a processor (e.g., a patient interface processor) for facilitating communication between the patient interface components 404a, 404b and the processor 518 of the controller 120. For example, the patient interface processor can allow the plurality of patient interface components to communicate with the medical device using a predetermined interface protocol. In some implementations, the patient interface processor is included in a portion of one or more of the patient interface components. In some implementations, the predetermined interface protocol is a controller area network (CAN) protocol. A CAN protocol is a bus standard that allows devices to communicate with each other in applications that might not include a host computer. In this way, the CAN protocol allows multiple nodes (e.g., the various patient interface components) to communicate with each other without each patient interface component needing to be connected to the controller 120.

The patient interface processor may be configured to perform one or more additional functions. For example, the patient interface processor can be configured to control the release of conductive gels (e.g., electrolytic gel) that can improve conduction of electrical current for sensing and/or treatment purposes. For example, conductive gel receptacles may be disposed in proximity to one of more therapy electrodes of a patient interface component (e.g., patient interface components 304a, 304b, 404a, 404b of FIGS. 3 and 4A-B).

Referring again to FIGS. 4A-4B, in some implementations, the patient interface processor can be configured to cause an alert to be provided by the wearable medical device 100. For example, the patient interface processor may be configured to cause a corresponding patient interface component 404a, 404b or the distribution node 430 to provide an alert prior to a treatment being applied to one of the patients. In some implementations, the patient interface components 404a, 404b, or the distribution node 430 can include a speaker for providing an audio alert and/or a vibration motor for providing a haptic alert.

It is appreciated that while in the foregoing a patient interface processor is described as initiating the alert and/or alarms as part of a treatment sequence, in some cases, the controller of the medical device (e.g., controller 120) may include alarm modules configured to initiate the alert and/or alarms corresponding to each of the patient interface components.

Figure 4B:
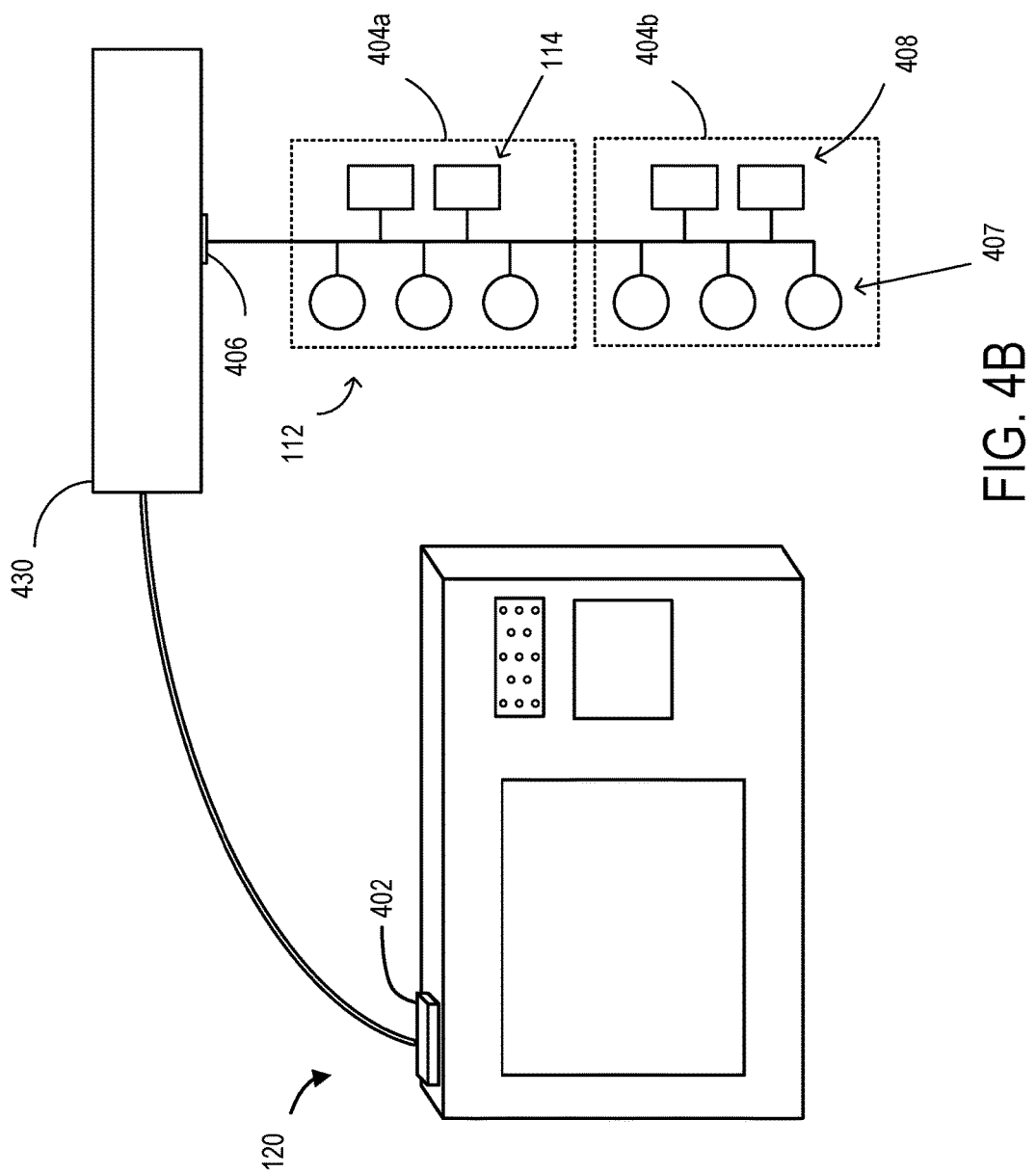

As mentioned above, in some implementations, one or more of the distribution nodes may be configured to accept connections to multiple patient interface components in series. FIG. 4B shows an example of the first and second patient interface component 404a, 404b connected to the distribution node 430 in series. The first patient interface component 404a is connected to the distribution node 430 via the port 406, and the second patient interface component 404b is connected to the first patient interface component 404a via a port on the first patient interface component 404a. The distribution node 430 may include a patient interface processor for facilitating communication between the connected patient interface components and the processor 518 of the controller 120. For example, the distribution node 430 may be configured to handle routing of power and/or control signals between the controller 120 and the one or more patient interface components 404a, 404b. For example, power may be supplied to each patient interface component 404a, 404b through power cables that run from the controller 120 and the distribution node 430 through the port 406.

In some implementations, as noted above, a battery may be included in the patient interface component 404a, 404b. As such, the battery may provide power to the other components in the patient interface component 404a, 404b. In such implementations, control signals may be routed via the port 406 to control the patient interface components 404a, 404b. If the patient interface component 404a, 404b includes a patient interface processor, then the control signals from the controller 120 may direct the patient interface processor in performing certain operations. For example, such operations may include retrieving the ECG signals from the patient, and/or initiating a treatment sequence if the situation arises.

In some implementations, the patient interface processor can allow the patient interface components 404a, 404b to communicate with the controller 120 using a predetermined interface protocol, such as a controller area network (CAN) protocol. Utilization of a CAN protocol can be especially useful when the patient interface components 404a, 404b are connected to the controller 120 via the distribution node 430 in series, as shown in FIG. 4B. While only two patient interface components 404a, 404b are shown in FIG. 4B, any number of patient interface components can similarly be connected in series. For example, a third patient interface component (e.g., for a third patient) may be connected to the second patient interface component 404b, a fourth patient interface component (e.g., for a fourth patient) may be connected to the third patient interface component, etc., such that all of the patient interface components are connected to the distribution node 430 in series. As described above, the distribution node 430 may be configured to handle the routing of power and/or control signals between the controller 120 and the patient interface components 404a, 404b. For example, in implementations in which a battery is not available in the patient interface components 404a, 404b, the distribution node 430 can determine which of the patient interface components 404a, 404b are connected to the controller 120 and/or enabled and provide power to the appropriate patient interface components. Similarly, the distribution node 430 can control the particular patient interface component(s) that control signals are received from and/or transmitted to. For example, the distribution node 430 may be configured to detect that the first patient interface component 404a is attached to a patient, and in response, provide sufficient power to the first patient interface component to allow the first patient interface component 404a to administer a treatment. Upon detecting that the second patient interface component 404b is attached to a patient, the distribution node 430 may be configured to at least partially reduce the power provided to the first patient interface component 404a and route additional power to the second patient interface component 404b to allow the second patient interface component 404b to administer a treatment. In some implementations, the port 402 on the controller 120 is a CAN bus, and the patient interface components that are connected in series are configured to communicate with the controller 120 using the CAN protocol.

Figure 5:
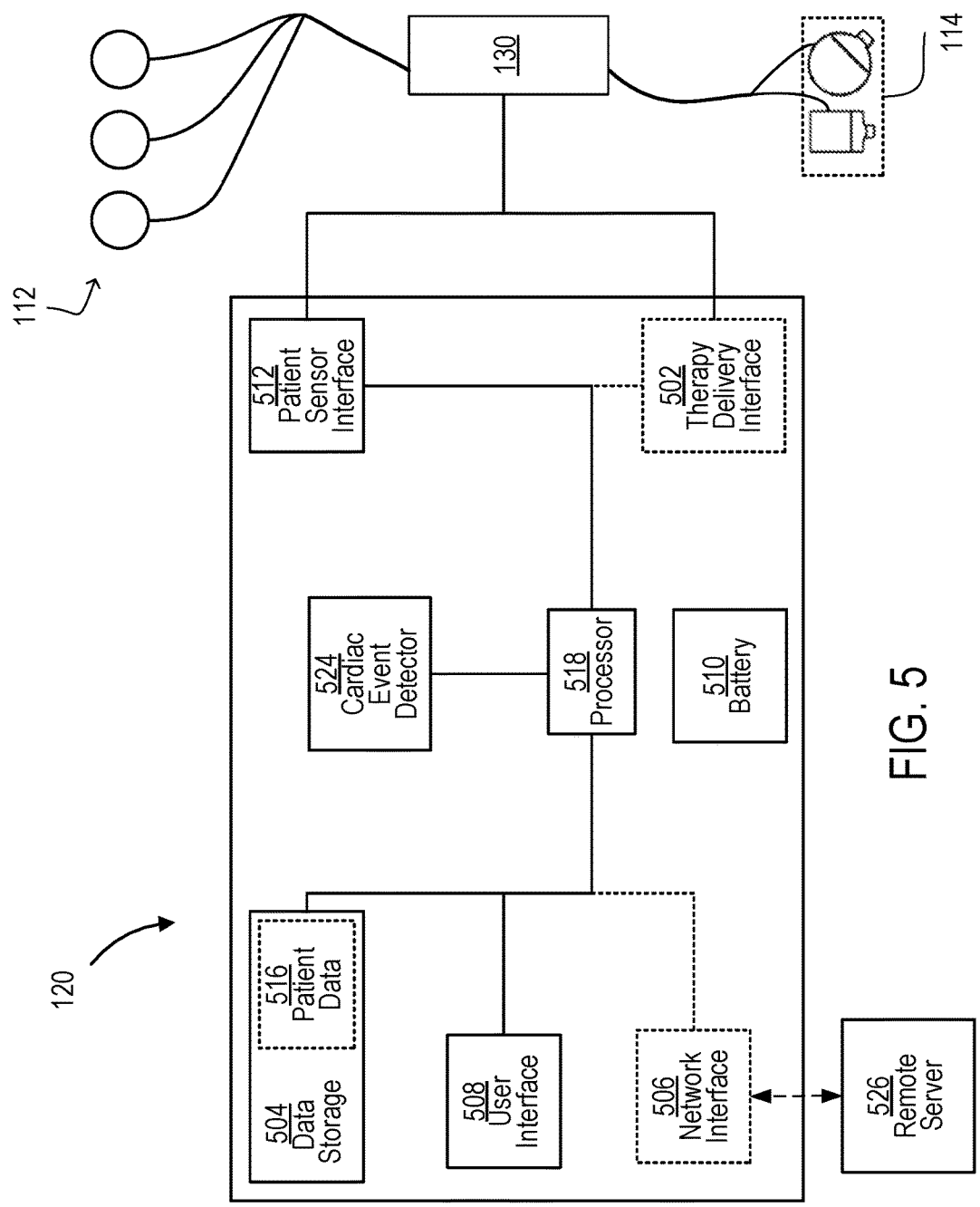
FIG. 5 is a functional schematic of the medical device controller.

FIG. 5 shows a schematic of an example of the medical device controller 120 of FIGS. 1, 2, and 4A-4B. The schematic for the medical device controller 320 of FIG. 3 may be substantially similar to the schematic shown in FIG. 5. The controller 120 includes a processor 518, a cardiac event detector 524, a patient sensor interface 512, an optional therapy delivery interface 502, data storage 504

(which may include patient data 516), an optional network interface 506, a user interface 508 (e.g., including the touch screen 220 shown in FIG. 2A), and a battery 510. The patient sensor interface 512 is coupled to the patient sensing electrodes 112 via the distribution node 130, and the therapy delivery interface 502 (if included) is coupled to the patient therapy or therapy electrodes 114 via the distribution node 130. The patient sensor interface 512 and the therapy delivery interface 502 implement a variety of coupling and communication techniques for facilitating the exchange of data between the patient electrodes 112, 114 and the controller 120.

In some implementations, the processor 518 can perform a series of instructions that control the operation of the other components of the controller 120. The cardiac event detector 524 is configured to monitor the cardiac activity of the patient and identify cardiac events experienced by the patient based on received cardiac signals. In some examples, the cardiac event detector 524 can access patient baseline information in the form of templates (e.g., which may be stored in the data storage 504 as patient data 516) that can assist the cardiac event detector 524 in identifying cardiac events experienced by the particular patient, as described above. The patient baseline information may correspond to the patient who is wearing the wearable medical device 100. In some implementations, the wearable medical device 100 may also be configured with baseline ECG recordings for persons who associate with the patient wearing the device 100 and who may, in the event of an emergency, need to be monitored by the device 100 (e.g., the patient's family members). For example, such baseline ECG recordings may be obtained during initial setup of the device. In some examples, the medical device may be configured to obtain and store ECG recordings corresponding to all persons in a household. In this way, the wearable medical device 100 can be used not only to treat strangers who the patient happens to come across by chance (e.g., as described above with reference to FIG. 2), but also to intimately monitor and/or treat additional patients whose baseline information is known to the device 100. Monitoring and/or treating patients with the aid of baseline information can provide for more accurate detection and treatment capabilities.

In some examples, the network interface 506 can facilitate the communication of information between the controller 120 and one or more other devices or entities over a communications network via either a wired or wireless connection. In some examples, the network interface 506 is configured to communicate with a server (e.g., a remote server 526). A medical service provider, such as a doctor, can access the data from the remote server 526 to access information related to one or more patients being monitored and/or treated by the wearable medical device 100, such that the medical service provider can remotely monitor the patients' medical conditions. In some implementations, the communication may occur via a telephone network or a cellular network (e.g., 2G, 3G, 4G), among others.

In some implementations, the wearable medical device 100 is capable of and designed for being worn by a patient who is at risk of developing cardiac problems, but who does not yet meet criteria to be outfitted with a medical device that includes a treatment component (e.g., a defibrillator). In such implementations, the controller 120 may omit the treatment components, including the therapy delivery interface 502 and the therapy electrodes 114. A wearable medical device 100 that does not include treatment components is sometimes referred to as a monitor (e.g., a cardiac monitor). The cardiac monitor may be prescribed so that continuous and/or event-based data can be sent from the cardiac monitor to a server (e.g., the remote server 526). A caregiver can access the data from the remote server 526 and determine whether the patient is experiencing or has experienced a cardiac problem. In some implementations, after determining that the patient is experiencing a cardiac problem, the caregiver may instruct the patient to begin wearing a medical device with treatment capabilities.

In some implementations, the device 100 may omit treatment components intended for the patient who is wearing the device 100, but may include treatment components intended for use on one or more other patients. For example, additional patient interface components (e.g., the second patient interface components 150, 304b, 404b of FIGS. 1-4B) may include therapy electrodes 204, 408.

Figure 6:
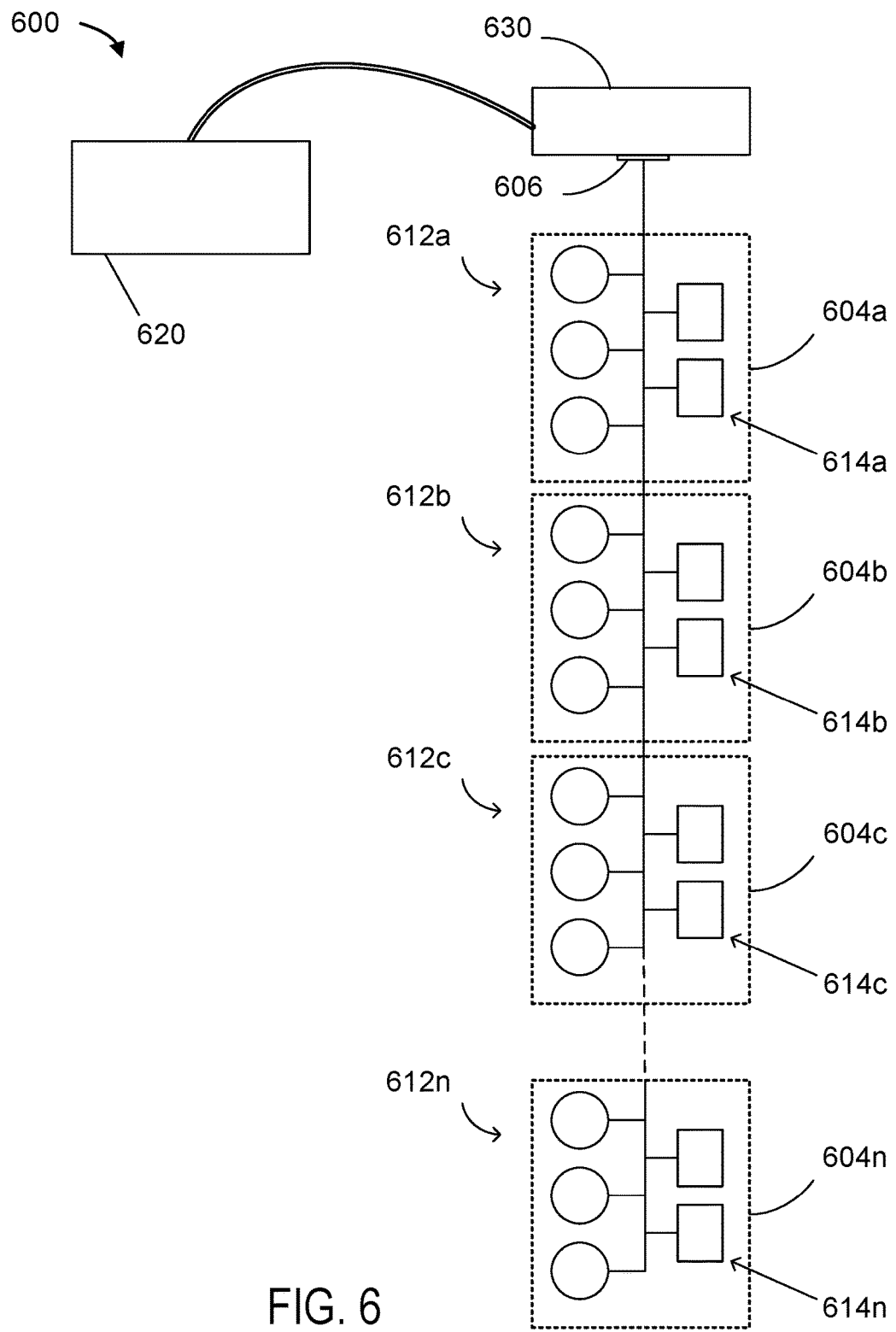
FIG. 6 shows an example of a wearable medical device that includes a plurality of patient interface components connected in series.

As described above, the medical device may include any number of patient interface components. FIG. 6 shows another example of a wearable medical device 600 that includes a plurality of patient interface components 604a-n. The patient interface components 604a-n are connected to a controller 620 via a port 606 on a distribution node 630. The first patient interface component 604a (e.g., for a first patient wearing the wearable medical device 600) is connected to the port 606 of the distribution node 630, the second patient interface component 604b (e.g., for a second patient) is connected to the first patient interface component 604a, the third patient interface component 604c (e.g., for a third patient) is connected to the second patient interface component 604b, and the remaining patient interface component (e.g., including the last patient interface component 604n of the series) are connected to the third patient interface component 604c, such that all of the patient interface components 604a-n are connected to the distribution node 630 in series. Such a series connection of components is sometimes referred to as a daisy chain. Like the distribution nodes described above, the distribution node 630 may be configured to handle the routing of power and/or control signals between the controller 620 and the patient interface components 604a-n. One or more of the patient interface components 604a-n can include sensing electrodes 612a-n and optional therapy electrodes 614a-n. In some implementations, some but not all of the patient interface components 604a-n include therapy electrodes 614a-n.

The distribution node 630 may include a processor (e.g., a patient interface processor) for facilitating communication between the patient interface components 902a-n and a processor of the controller 620 (e.g., a processor substantially similar to the processor 518 of FIG. 5). For example, the patient interface processor can allow the patient interface components 604a-n to communicate with the controller 620 using a predetermined interface protocol, such as a CAN protocol. In some implementations, the patient interface processor is included in a portion of one or more of the patient interface components 604a-n.

While only four patient interface components 604a-n are shown in FIG. 6, additional patient interface components may be connected in series to the last patient interface component 604n in the daisy chain. Thus, the daisy chain configuration can provide the flexibility for incorporation of additional patient interface components without needing to disconnect and/or depower the other patient interface components. In this way, additional patient interface components can be added on-demand as needed. The patient interface processor of the distribution node 630 may be configured to accommodate such additional patient interface components seamlessly (e.g., without interruption of the operation of the other patient interface components 604a-n).

In some implementations, one or more of the patient interface components 604*a-n* may be configured to be affixed to a garment (e.g., such as the garment 110 of FIG. 1). For example, the sensing electrodes 612*a* and/or the therapy electrodes 614*a* of the first patient interface component 604*a* may be affixed to a garment at appropriate positions, and the garment can be worn by the first patient as the first patient goes about his or her daily routine. Upon encountering a person who may be experiencing a cardiac event, rather than directly applying the second patient interface component 604*b* to the second patient, the sensing electrodes 612*b* and/or the therapy electrodes 614*b* of the second patient interface component 604*b* may be affixed to a second garment, and the second garment may be placed on the second patient. Utilizing a garment to aid in affixing the electrodes to the second patient can free up the first patient from otherwise needing to manually keep the electrodes applied, thereby allowing the first patient to engage in other life-saving activities (e.g., performing CPR, placing a call to emergency medical services, etc.).

Alternative Implementations

While certain implementations have been described, other implementations are possible.

While the wearable medical device has been largely described as including one or more patient interface components, one or more garments, and a medical device controller, the wearable medical device can take other forms, e.g., one or more of the components of the type of wearable medical device described herein may be omitted in other types of wearable medical devices. For example, in some implementations, the wearable medical device itself does not include a garment and/or a controller. Rather, the wearable medical device may be configured to connect to and/or communicate with the garment and/or the controller. In this way, the garment(s) and/or the controller may be separate components from the wearable medical device.

While some of the patient interface components have been described as including both sensing electrodes and treatment electrodes, in some implementations, one or more of the patient interface components described herein may omit the sensing electrodes or the treatment electrodes. For example, a patient interface component configured to monitor a patient without providing treatment capabilities may omit the therapy electrodes. Thus, the therapy electrodes may be optional.

In some implementations, the wearable medical device may be configured to operate in multiple modes. For example, the wearable medical device (e.g., a LifeVest® wearable defibrillator) may be configured to operate in a first mode by default. While operating in the first mode, the wearable medical device may be largely configured to monitor physiological signals of the patient who is wearing the device and/or provide necessary treatments to the patient. The wearable medical device may also be configured to operate in a second mode in which the device is configured to monitor physiological signals of one or more additional patients and/or provide necessary treatments to the additional patients. In the second operating mode, the wearable medical device may still be configured to monitor and/or treat the patient who is wearing the device. That is, the second operating mode may include the features of the first operating mode. The second operating mode may be referred to as "Automated External Defibrillator (AED) mode."

In some implementations, the user interface of the medical device controller may adapt based on the mode under which the device is operating. For example, when the wearable medical device is operating in the first (e.g., default) mode, the user interface may present information that is relevant only to the patient who is wearing the device. Similarly, under the first operating mode, the controller may be configured to accept inputs (e.g., via the touch screen) for controlling aspects of the monitoring and/or treatment functions that apply to the patient wearing the device. When the wearable medical device is operating in the second (e.g., AED) mode, the user interface may present information that is relevant to both the patient wearing the device and one or more additional patients who may be monitored and/or treatment by the device. For example, the touch screen may present instructions for assisting a user in placing the patient interface component in contact with the one or more additional patients in order to monitor and/or treat the additional patients.

In some implementations, the wearable medical device may enter the AED operating mode upon a patient interface component being connected to the monitor. For example, the user interface may present an AED interface and be configured to receive inputs related to an AED treatment upon a patient interface component (e.g., an additional patient interface component) being connected to the monitor, another port of the distribution node, and/or a patient interface component (e.g., in a series connection).

In some implementations, the wearable medical device may enter the AED operating mode upon a particular type of patient interface component being connected to the monitor. The patient interface component may include one or more OneStep™ electrodes that are configured to provide defibrillation, pacing, and/or CPR assistance to the user, and the wearable medical device may enter the AED operating mode upon connection of a OneStep™ electrode. The OneStep™ electrodes and/or the user interface of the monitor may be configured to assist the user in performing CPR on the one or more additional patients. For example, the OneStep™ electrodes may include a CPR sensor that is configured to measure information related to rate and/or depth of CPR compressions administered to the patient. The CPR sensor may include one or more accelerometers and/or a gyroscope for measuring motion data. When the OneStep™ electrodes are connected to the monitor, the monitor may be configured to provide visual and/or verbal cues for coaching the user performing the CPR.

In some implementations, the OneStep™ electrodes include a condition sensor for monitoring the condition of the electrodes. If it is determined that a therapy may be compromised by a suboptimal condition of the electrodes, the monitor may provide an alert indicating such. The monitor may also be configured to provide an alert when an expiration date of the electrodes is approaching.

As described above with reference to FIG. 2, the patient who is wearing the wearable medical device may remove the wearable medical device from himself or herself before attending to the second patient. In some implementations, a portion of the medical device other than the second patient interface component may include one or more electrodes (e.g., one or more sensing electrodes and/or one or more therapy electrodes) that can be affixed to the second patient for monitoring the patient and/or delivering a treatment. For example, a surface of the medical device, such as a back surface of the medical device controller, may include one or more sensing electrodes and/or one or more therapy electrodes that can be put in contact with the second patient. For example, the first patient may remove the controller from the garment and hold the electrode(s) against the second patient (e.g., against the second patient's chest) for monitoring and/or treatment purposes.

In some implementations, a surface of the garment (e.g., a back surface of the garment) may include one or more sensing electrodes and/or one or more therapy electrodes that can be put in contact with the second patient. For example, the first patient may remove the garment from himself or herself and hold the electrode(s) against the second patient for monitoring and/or treatment. The electrode(s) may be used in addition to or instead of the electrodes of the second patient interface component. For example, the garment may be placed on top of the second patient such that the electrode(s) make contact with the patient's chest. In some examples, the garment may be placed underneath the second patient such that the electrode (s) make contact with the second patient's back, and one or more other electrodes (e.g., electrode(s) of the second patient interface component) may be placed on the second patient's chest. In some implementations, the first patient does not need to remove the medical device in order to position the electrode(s) in contact with the second patient.

While we have described the electrodes for monitoring and/or treating the second patient as being different than those used for treating the first patient, in some implementations, the same electrodes that are configured to monitor and/or treat the first patient may also be used to monitor and/or treat the second patient. For example, the first patient interface component may be configured to be removed from the first patient and affixed to the second patient (e.g., temporarily). In particular, the sensing electrodes and/or the therapy electrodes that are affixed to the garment of the medical device may be temporarily removed from the garment and affixed to the second patient for monitoring and/or treatment purposes. Once monitoring and/or treatment have concluded, the electrodes may be reaffixed to the garment for monitoring and/or treating the first patient.

As described above, the medical device determines whether the patient may be experiencing a cardiac condition based on one or more detection parameters (e.g., conditions), and such detection parameters may depend on the mode that the medical device is operating under at the time. One example of a detection parameter that is described above is related to the power spectral density (PSD) of a cardiac signal (e.g., an ECG signal). However, other detection parameters can be used instead of or in addition to the PSD. For example, one or more of the detection parameters can be related to other components of the patient's ECG signal, such as waveform shape variations (e.g., QRS shape), duration variations (e.g., QRS or T-wave width, ST segment width), amplitude variations (e.g., R wave or T-wave amplitude), period variations (e.g., R-R interval, QT interval, ST interval), T wave alternans (TWA), heart rate variability (HRV), heart rate turbulence (HRT), PR interval, slurring of the QRS complex, premature ventricular contraction (PVC), frequency analysis, a VT or VF template, QT variability, QT interval length, and/or combinations and/or ratios of the aforementioned.

While the medical device has been largely described as being configured to monitor and treat cardiac condition, other conditions can also be monitored and/or treated. For example, in some implementations, the medical device can include one or more sensors for determining a blood sugar content of a patient (e.g., a first patient who is wearing the medical device and/or one or more additional patients). For example, the medical device may include a glucose sensor (e.g., an invasive glucose sensor or a non-invasive glucose sensor such as an infrared sensor, an ultrasound, and/or a dielectric spectroscopy device) that can determine the sugar content of a second patient's blood. The first patient may encounter a second patient who appears to be experiencing a medical condition. The first patient can use the glucose sensor to test the sugar content of the second patient's blood, and the medical device can determine whether the second patient has an abnormal sugar content. The medical device may be equipped with a component for treating the abnormal blood sugar condition. For example, the medical device may include an insulin delivery device for regulating the second patient's abnormal blood sugar content.

Example Infrastructure

Software running on the medical device controller (e.g., the controller 120, 320, 620 of FIGS. 1-6) can be realized by instructions that upon execution cause one or more processing devices to carry out the processes and functions described above. The instructions can include, for example, interpreted instructions such as script instructions, or executable code, or other instructions stored in a computer readable medium.

A server (e.g., the remote server 526 of FIG. 5) can be distributively implemented over a network, such as a server farm, or a set of widely distributed servers or can be implemented in a single virtual device that includes multiple distributed devices that operate in coordination with one another. For example, one of the devices can control the other devices, or the devices may operate under a set of coordinated rules or protocols, or the devices may be coordinated in another fashion. The coordinated operation of the multiple distributed devices presents the appearance of operating as a single device.

In some examples, the components of the controller may be contained within a single integrated circuit package. A system of this kind, in which both a processor (e.g., the processor 518 of FIG. 5) and one or more other components (e.g., the cardiac event detector 524) are contained within a single integrated circuit package and/or fabricated as a single integrated circuit, is sometimes called a microcontroller. In some implementations, the integrated circuit package includes pins that correspond to input/output ports (e.g., that can be used to communicate signals to and from one or more of the input/output interface devices).

Although an example processing system has been described above, implementations of the subject matter and the functional operations described above can be implemented in other types of digital electronic circuitry, or in computer software, firmware, or hardware, including the structures disclosed in this specification and their structural equivalents, or in combinations of one or more of them. Implementations of the subject matter described in this specification, such as storing, maintaining, and displaying artifacts can be implemented as one or more computer program products, i.e., one or more modules of computer program instructions encoded on a tangible program carrier, for example a computer-readable medium (e.g., the data storage 504 of FIG. 5), for execution by, or to control the operation of, a processing system. The computer readable medium can be a machine readable storage device, a machine readable storage substrate, a memory device, or a combination of one or more of them.

The term "system" may encompass all apparatus, devices, and machines for processing data, including by way of example a programmable processor, a computer, or multiple processors or computers. A processing system can include, in addition to hardware, code that creates an execution environment for the computer program in question, e.g., code that constitutes processor firmware, a protocol stack, a database management system, an operating system, or a combination of one or more of them. In some implementations, operating systems can include a Windows based operating system, OSX, or other operating systems.

A computer program (also known as a program, software, software application, script, executable logic, or code) can be written in any form of programming language, including compiled or interpreted languages, or declarative or procedural languages, and can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Computer readable media suitable for storing computer program instructions and data include all forms of non-volatile or volatile memory, media and memory devices, including by way of example semiconductor memory devices, e.g., EPROM, EEPROM, and flash memory devices; magnetic disks, e.g., internal hard disks or removable disks or magnetic tapes; magneto optical disks; and CD-ROM, DVD-ROM, and Blu-Ray disks. The processor and the memory can be supplemented by, or incorporated in, special purpose logic circuitry. Sometimes a server (e.g., the remote server 526 of FIG. 5) is a general purpose computer, and sometimes it is a custom-tailored special purpose electronic device, and sometimes it is a combination of these things. Implementations can include a back end component, e.g., a data server, or a middleware component, e.g., an application server, or a front end component, e.g., a client computer having a graphical user interface or a Web browser through which a user can interact with an implementation of the subject matter described is this specification, or any combination of one or more such back end, middleware, or front end components. The components of the system can be interconnected by any form or medium of digital data communication, e.g., a communication network such as the connection between the remote server 526 and the network interface 506, as shown in FIG. 5. Examples of communication networks include a local area network ("LAN") and a wide area network ("WAN"), e.g., the Internet.

Having described several aspects of at least one example of this disclosure, the examples of the methods and apparatuses discussed herein are not limited in application to the details of construction and the arrangement of components set forth in this description or illustrated in the accompanying drawings. The methods and apparatuses are capable of implementation in other examples and of being practiced or of being carried out in various ways. Examples of specific implementations are provided herein for illustrative purposes only and are not intended to be limiting. In particular, acts, elements and features discussed in connection with any one or more examples are not intended to be excluded from a similar role in any other examples. Accordingly, the foregoing description and drawings are by way of example only Also, the phraseology and terminology used herein is for the purpose of description and should not be regarded as limiting. Any references to examples or elements or acts of the systems and methods herein referred to in the singular may also embrace examples including a plurality of these elements, and any references in plural to any example or element or act herein may also embrace examples including only a single element. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms.

What is claimed is:

1. A wearable medical device comprising:
   a plurality of patient interface components each configured to be in physical contact with a body of each of a plurality of patients;
   a first patient interface component of the plurality of patient interface components, the first patient interface component comprising
      a plurality of first sensing electrodes for receiving one or more signals from a first patient of the plurality of patients, and
      a plurality of first therapy electrodes for delivering a first defibrillating shock to the body of the first patient;
   a second patient interface component of the plurality of patient interface components, the second patient interface component comprising
      a plurality of second sensing electrodes for receiving one or more signals from a second patient of the plurality of patients; and
   a medical device controller comprising
      a plurality of ports disposed on the medical device controller, wherein the first patient interface component is configured to connect to a first one of the plurality of ports disposed on the medical device controller and the second patient interface component is configured to connect to a second one of the plurality of ports disposed on the medical device controller, and
      one or more processors in communication with the plurality of patient interface components, the one or more processors configured to
         detect a first arrhythmia condition of the first patient based at least in part on the one or more signals from the first patient,
         cause the first defibrillating shock to be delivered to the first patient, wherein the first defibrillating shock is based at least in part on the detected first arrhythmia condition of the first patient, and
         detect a second arrhythmia condition of the second patient based at least in part on the one or more signals from the second patient.

2. The wearable medical device of claim 1, comprising a plurality of garments, each garment for affixing one of the plurality of patient interface components to the body of a corresponding patient.

3. The wearable medical device of claim 1, comprising an electrode patch that includes at least one of the plurality of first sensing electrodes and at least one of the plurality of first therapy electrodes.

4. The wearable medical device of claim 1, wherein at least one of the plurality of first sensing electrodes, the plurality of second sensing electrodes, and the plurality of first therapy electrodes is configured to be disposable.

5. The wearable medical device of claim 1, comprising a garment for affixing the first patient interface component to the body of the first patient, wherein the garment includes a compartment configured for storing one or both of the plurality of second sensing electrodes and a plurality of second therapy electrodes.

6. The wearable medical device of claim 1, wherein the second patient interface component comprises a plurality of second therapy electrodes for delivering a second defibrillating shock to the second patient.

7. The wearable medical device of claim 6, comprising a user interface configured for
receiving input and providing information related to one or both of the first arrhythmia condition and the first defibrillating shock, and
receiving input and providing information related to one or both of the second arrhythmia condition and the second defibrillating shock.

8. The wearable medical device of claim 7, wherein the user interface is configured for providing the information related to one or both of the second arrhythmia condition and the second defibrillating shock when the second patient interface component is in communication with the one or more processors.

9. The wearable medical device of claim 6, wherein each of the first and second patient interface components comprises a patient interface processor.

10. The wearable medical device of claim 9, wherein each of the first and second patient interface components includes one or more capacitors for storing electrical energy for use by the plurality of first and second therapy electrodes for delivering the first and second defibrillating shocks to the first and second patients.

11. The wearable medical device of claim 10, wherein first and second patient interface processors are each configured to provide an alert prior to delivering the first and second defibrillating shocks.

12. The wearable medical device of claim 11, wherein the alert is a haptic alert.

13. A wearable medical device comprising:
a plurality of patient interface components each configured to be in physical contact with a body of each of a plurality of patients;
a first patient interface component of the plurality of patient interface components, the first patient interface component comprising
a plurality of first sensing electrodes for receiving one or more signals from a first patient of the plurality of patients, and
a plurality of first therapy electrodes for delivering a first defibrillating shock to the body of the first patient;
a second patient interface component of the plurality of patient interface components, the second patient interface component comprising
a plurality of second sensing electrodes for receiving one or more signals from a second patient of the plurality of patients; and
a medical device controller comprising
a port for connecting the plurality of patient interface components to the medical device controller, wherein the first patient interface component is configured to connect to the port, and the second patient interface component is configured to connect to the first patient interface component in series, and
one or more processors in communication with the plurality of patient interface components, the one or more processors configured to
detect a first condition of the first patient based at least in part on the one or more signals from the first patient,
cause the first defibrillating shock to be delivered to the first patient, wherein the first defibrillating shock is based at least in part on the detected first arrhythmia condition of the first patient, and
detect a second arrhythmia condition of the second patient based at least in part on the one or more signals from the second patient.

14. The wearable medical device of claim 13, wherein the port comprises a CAN bus.

15. The wearable medical device of claim 13, further comprising a distribution node configured to connect to the port of the medical device controller, the distribution node comprising a patient interface processor.

16. The wearable medical device of claim 13, further comprising a patient interface processor configured to process the one or more signals received by the plurality of first and second sensing electrodes.

17. The wearable medical device of claim 13, further comprising a patient interface processor configured to cause a conductive gel to be released by the plurality of first therapy electrodes prior to the first defibrillating shock being delivered.

18. The wearable medical device of claim 13, further comprising a patient interface processor configured to provide an alert to the first patient prior to the first defibrillating shock being delivered.

19. The wearable medical device of claim 15, wherein each of the plurality of patient interface components is configured to connect to the distribution node in series.

20. The wearable medical device of claim 13, further comprising a plurality of patient interface processors, each one of the plurality of patient interface processors being associated with a corresponding one of the plurality of patient interface components and configured to facilitate communication between the plurality of patient interface components and the one or more processors of the medical device controller.

21. The wearable medical device of claim 20, wherein the plurality of patient interface components and the one or more processors communicate using a controller area network (CAN) protocol.

* * * * *